US007009071B2

(12) United States Patent
Dabak et al.

(10) Patent No.: US 7,009,071 B2
(45) Date of Patent: Mar. 7, 2006

(54) PROCESS FOR THE PREPARATION OF 4-AMINO-1-HYDROXYBUTYLIDENE-1, 1-BIPHOSPHONIC ACID

(75) Inventors: Kadir Dabak, Istanbul (TR); A. Evren Ozarslan, Istanbul (TR); Filiz Sahbaz, Istanbul (TR); Tuncer Aslan, Istanbul (TR)

(73) Assignee: Eos Eczacibasi Ozgun Kimyasal Urunler Sanayi Ve Ticaret A.S., Istanbul (TR)

( * ) Notice: Subject to any disclaimer, the term of this patent is extended or adjusted under 35 U.S.C. 154(b) by 207 days.

(21) Appl. No.: 10/473,600

(22) PCT Filed: May 8, 2002

(86) PCT No.: PCT/TR02/00018

§ 371 (c)(1),
(2), (4) Date: Oct. 10, 2003

(87) PCT Pub. No.: WO02/090367

PCT Pub. Date: Nov. 14, 2002

(65) Prior Publication Data

US 2004/0152916 A1 Aug. 5, 2004

(30) Foreign Application Priority Data

May 10, 2001 (TR) ..................................... a 2001/01250

(51) Int. Cl.
*C07C 229/01* (2006.01)
*C07C 225/163* (2006.01)

(52) U.S. Cl. ................. 562/13; 562/8; 562/11

(58) Field of Classification Search ............... 562/8, 562/11, 13
See application file for complete search history.

(56) References Cited

U.S. PATENT DOCUMENTS

| 4,407,761 | A | * | 10/1983 | Blum et al. | ............ 562/13 |
| 4,624,947 | A | * | 11/1986 | Blum et al. | ............ 514/108 |
| 4,705,651 | A | * | 11/1987 | Staibano | ............ 562/13 |
| 4,922,007 | A | * | 5/1990 | Kieczykowski et al. | ............ 562/13 |
| 5,019,651 | A | * | 5/1991 | Kieczykowski | ............ 562/13 |
| 5,162,310 | A | * | 11/1992 | Jaeggi | ............ 562/13 |
| 5,908,959 | A | * | 6/1999 | Kubela et al. | ............ 562/13 |
| 6,201,148 | B1 | * | 3/2001 | Lidor-Hadas et al. | ............ 562/13 |

FOREIGN PATENT DOCUMENTS

WO    WO 98 34940    8/1998

\* cited by examiner

*Primary Examiner*—Johann Richter
*Assistant Examiner*—Lansana Nyalley
(74) *Attorney, Agent, or Firm*—Arent Fox PLLC

(57) ABSTRACT

This invention is related with the preparation of 4-amino-1-hydroxybutylidene-1,1-biphosphonic acid or salts thereof. The reaction of 4-aminobutyric acid with phosphorous acid and phosphorus trichloride in the presence of aralkyl or alkyl ethoxylates or triglycerides such as plant or animal oils or their derivatives; and recovering of 4-amino-1-hydroxybutylidene-1,1-biphosphonic acid or salts thereof are described. The main feature of the invention is in the use of the above defined non-ionic emulgators in the phosphonylation reaction.

15 Claims, No Drawings

PROCESS FOR THE PREPARATION OF 4-AMINO-1-HYDROXYBUTYLIDENE-1, 1-BIPHOSPHONIC ACID

CROSS-REFERENCE TO RELATED APPLICATION

This application is a National Stage entry of International Application No. PCT/TR02/00018 filed May 8, 2002. the entire specification claims and drawings of which are incorporated herewith by reference.

This invention is related with the preparation of 4-amino-1-hydroxybutylidene-1,1-biphosphonic acid or salts thereof. The reaction of 4-aminobutyric acid with phosphorous acid and phosphorus trichloride in the presence of aralkyl or alkyl ethoxylates or triglycerides such as plant or animal oils or their derivatives and recovering of 4-amino-1-hydroxybutylidene-1,1-biphosphonic acid or salts thereof are described.

4-Amino-1-hydroxybutylidene-1,1-biphosphonic acid monosodium salt trihydrate is used for treatment or prevent of diseases involving bone disorders, such as hypercalcemia of malignanch, Paget's disease and osteoporosis.

4-Amino-1-hydroxybutylidene-1,1-biphosphonic acid or salts thereof are prepared basically by the reaction of 4-aminobutryic acid with a mixture of phosphorous acid and one of the three phosphorus chlorides; phosphorous trichloride, phosphorous oxychloride or phosphorous pentachloride and then quenching the reaction mixture with water followed by heating to hydrolyse the phosphorous intermediates.

Several patented methods can be found in the literature for the preparation of ω-amino-1-hydroxyalkylidene-1,1-bisphosphonic acids and especially for 4-amino-1-hydroxybutylidene-1,1-biphosphonic acid and salts thereof. In U.S. Pat. No. 4,407,761 (Blom et al.) the preparation of 4-amino-1-hydroxybutylidene-1,1-biphosphonic acid besides other bisphosphonic acids are described. When using this procedure, a semisolid sticky non-stirrable mass develops which prevents smooth heat transfer. The described process might be suitable for laboratory preparations, however for industrial production it is not acceptable. In U.S. Pat. No. 4,705,651 (Staibano, G.), a similar procedure is followed with different molar ratios and although some improvements were achieved, it is still unsuitable for industrial scale up.

Kieczykowski et al. (In U.S. Pat. Nos. 4,922,007; 5,019,651 and J. Org. Chem. 1995, 60, 8310–8312) reported that the solidification problem has been solved: Methanesulfonic acid was used to solubilize the reaction components and keep them fluid throughout. By the use of methanesulfonic acid, the fluidity problems were solved however another serious safety problem surfaced. A reaction between methanesulfonic acid and phosphorus trichloride is exothermic and at certain point becomes uncontrollable.

U.S. Pat. No. 5,908,959 (Kubela et al.) also describes the preparation of 4-amino-1-hydroxybutylidene-1,1-biphosphonic acid or salts thereof. The reaction is carried out in poly(alkylene glycol) as a diluent, which solubilizes the reaction components, however still when the reaction mixture is decomposed with water, an agitation problem occurs. The viscous reaction mixture must be transferred into the water. To facilitate this, viscosity problem is solved by the addition of toluene. When using toluene, a safety problem arises and also an additional separation step is needed.

In the present invention; by the use of aralkyl or alkyl ethoxylates or triglycerides such as plant or animal oils or their derivatives as emulgators, the solidification and the safety problems are solved in a cheaper, safer and easily accessible way without any need of an additional solvent. These emulgators solubilize the reaction components and do not react with the reactants to cause any uncontrolled reactions. It has been found that 4-amino-1-hydroxybutylidene-1,1-biphosphonic acid or its salts can be obtained in a safe and high yielded way without an additional purification step.

Aralkyl or alkyl ethoxylates or their derivatives are used very often in the textile, leather and metal industries as emulgators. Triglycerides such as plant or animal oils are also used very often in the food and lubricant industries. These emulgators are easily accessible, readily available and non-expensive.

The reaction of 4-aminobutyric acid with phosphorous acid and phosphorus trichloride in the presence of one of these emulgators at a suitable temperature such as between about 40° C. and about 150° C.; and hydrolysing the phosphorous intermediates by heating the reaction mixture in the presence of water and recovering of 4-amino-1-hydroxybutylidene-1,1-biphosphonic acid or salts thereof are described.

Aralkyl or alkyl ethoxylates or their derivatives may be selected from the general formula of R—X—O—$(CH_2CH_2O)_n$—H; and triglycerides might be selected from the general formula of $(RCO_2CH_2)_2$CHCOOR wherein R represents branched or non-branched alkyl groups which contain 1 to 20 carbon atoms, X represents phenyl or naphtyl or —$CH_2$— groups and; n is a number of between 1 and about 30.

The main feature of the invention is in the use of the above defined emulsifiers or derivatives thereof in the phosphonylation reaction. These compounds keep the mixture in homogenous form and can be separated easily from the product at the end of the reaction and can be reused. The hydrolysis of the formed phosphorous intermediates can be completed in the same reaction mixture and if desired, by adjusting the pH to about 4.3, the sodium salt of the said biphosphonic acid can be directly obtained and isolated in a pure form.

The 4-aminobutyric acid and the phosphorous acid are suspended in one of the mentioned emulgators and reacted with phosphorus trichloride at a suitable temperature for example between about 40° C. and about 150° C., preferably at about 70° C. The phosphonylation reaction is completed in about 3 hours at this temperature. The preferred ratio of the amino acid to phosphorous acid and to phosphorous trichloride is about 1:1:2.

As example of aralkyl or alkyl ethoxylates or their derivatives, which can be applied, are nonylphenol with 4 mol, 6 mol or 10 mol ethoxylate; and alkyl ethoxylates such as lauryl alcohol of different ethoxylate numbers. And as example of triglycerids are sunflower oil, olive oil and corn oil, which are glyceride of oleic acid, palmitic acid, lineloic acid, stearic acid, myristic acid, behenic acid and arachidic acid in different ratios.

The reaction can be shown schematically as follows:

SCHEME

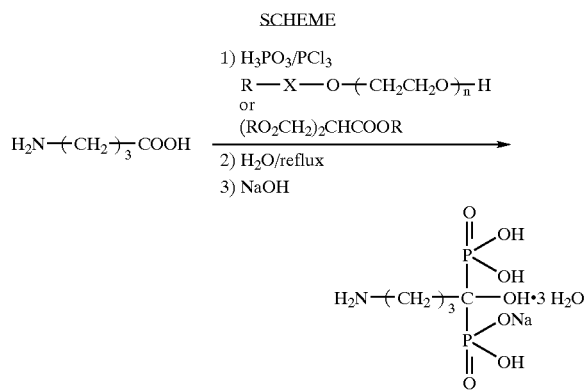

Where in R represents branched or non-branched alkyl groups which contain 1 to 20 carbon atoms, X represents phenyl or naphtyl or —$CH_2$— groups and; n is a number of between 1 and about 30.

The following examples are introduced the practical procedures and the results without any limitations in any subject.

EXAMPLE 1

Preparation of 4-amino-1-hydroxybutylidene-1,1-biphosphonic Acid Monosodium Salt Trihydrate in Nonylphenol Ethoxylate 4 Mol (NP4) (or in Nonylphenol Ethoxylate 6 Mol)

A 2-L flask charged with 500 mL of NP 4 (or Nonylphenol Ethoxylate 6 Mol), 75.4 g (0.73 mol) of 4-aminobutyric acid and 60 g (0.73 mol) of phosphorous acid in room temperature. The system was connected to a caustic scrubber and flushed with nitrogen. After 15 minutes of stirring, 132 mL of phosphorous trichloride was added by dropwise addition over a period of 30 minutes. Then the reaction mixture was stirred at 70° C. for 4 hours. After 4 hours, the mixture was cooled to 20° C., then 300 mL of water was added by dropwise addition over a period of 30 minutes. After completion of the addition of the water, the reaction mixture was heated at 105° C. for 4 hours, then cooled to 20° C. The stirring was discontinued to allow the layers separate, the lower aqueous layer was separated and the pH of this solution was adjusted to 4.3 with 50% NaOH. After strirring for 13 hours, 50 mL of acetone was added and stirred for 1 hr, then the crystalline product was collected by filtration, washed with 100 mL of ice cold water and 100 mL of acetone and dried at room temperature. The yield of 4-amino-1-hydroxybutylidene-1,1-biphosphonic acid monosodium salt trihydrate was 136.5 g (57.4%. The analysis confirmed the identity of the product and the absence of impurities.

$^{32}$P-NMR, $^1$H-NMR and $^{13}$C-NMR analyses were recorded on a Varian Mercury 300 MHz instrument.

$^{32}$P-NMR ($D_2O$), 18.794 (s); $^{13}$C-NMR ($D_2O$), 30.68 (t), 40.07(t), 73.59 (s); $^1$H-NMR ($D_2O$), 1.84 (4H, m), 2.87 (2H, m).

EXAMPLE 2

Preparation of 4-amino-1-hydroxybutylidene-1,1-biphosphonic Acid Monosodium Salt Trihydrate in Nonylphenol Ethoxylate 10 Mol Instead of NP4, NP10 was used as a solvent and a procedure was followed as described in Example 1 until 4-hour hydrolysis at about 110° C. and cooling to room temperature. Then pH of all the reaction mixture (because two phases were not formed at this point as described in example 1.) was adjusted to 4.3 and then two phases were formed. The lower phase was separated, after strirring for 13 hours, 50 mL of acetone was added and stirred for 1 hr. Precipitated crystalline product was collected by filtration, washed with 100 mL of ice cold water, 100 mL of acetone and dried at room temperature. The analysis confirmed the identity of the product and the absence of impurities. The yield of 4-amino-1-hydroxybutylidene-1,1-biphosphonic acid monosodium salt trihydrate was 58%.

EXAMPLE 3

Preparation of 4-amino-1-hydroxybutylidene-1,1-biphosphonic Acid in Nonylphenol Ethoxylate 4 Mol (or in Nonylphenol Ethoxylate 6 Mol)

A procedure was followed as described in Example 1 until 4-hour hydrolysis at about 110° C. and cooling to room temperature. Then stirring was discontinued to allow the layers separate, the lower aqueous layer was separated and 500 mL of acetone was added and stirred. The product firstly was separated as in oil form then was crystallised after 10 minutes stirring. The crystalline product was collected by filtration, washed with 100 mL of ice cold water and 100 mL of acetone and dried at room temperature. The yield of 4-amino-1-hydroxybutylidene-1,1-biphosphonic Acid was 60%. 1 L of acetone was added to the upper layer and the yield was increased from 60 to 65% by the filtration of precipitated product however since this second precept was not as pure as the first one, it needs an additional crystallisation. The analysis confirmed the identity of the product and the absence of impurities.

EXAMPLE 4

Preparation of 4-amino-1-hydroxybutylidene-1,1-biphosphonic Acid in Nonylphenol Ethoxylate 10 Mol Instead of NP4, NP10 was used as a solvent and a procedure was followed as described in Example 1 until 4-hour hydrolysis at about 110° C. and cooling to room temperature. Then 1.5 L of acetone was added and stirred, the product firstly was separated as in oil form then was crystallised after 10 minutes stirring. The crystalline product was collected by filtration, washed with 250 mL of ice cold water and 250 mL of acetone and dried at room temperature. The yield of 4-amino-1-hydroxybutylidene-1,1-biphosphonic Acid was 60%. The analysis confirmed the identity of the product and the absence of impurities.

EXAMPLE 5

Preparation of 4-amino-1-hydroxybutylidene-1,1-biphosphonic Acid Monosodium Salt Trihydrate in Lauryl alcohol Ethoxylate 6 Mol Instead of NP4, lauryl alcohol Ethoxylate 6 Mol was used and an experiment was carried out same as it was described in Example 1. The yield of 4-amino-1-hydroxybutylidene-1,1-biphosphonic Acid Monosodium Salt Trihydrate was (59%). The analysis confirmed the identity of the product and the absence of impurities.

EXAMPLE 6

Preparation of 4-Amino-1-hydroxbutylidene-1,1-bisphosphonic acid monosodium salt trihydrate by using sunflower oil.

A 3 L flask was equipped with a mechanical stirrer, thermometer, condenser, and an addition funnel. The system was connected to a caustic scrubber and flushed with nitrogen. The flask was charged with 500 mL of sunflower oil. The temperature was brought to 75° C. At this temperature 100 g (0.97 mol) of 4-aminobutyric acid and 79.5 g (0.97 mol) of phosphorous acid were added. The mixture was stirred for 15 minutes. Phosphorous trichloride 130 mL (1.45 mol) was added to this solution in 20 minutes by keeping the internal temperature between 70 to 75° C. The mixture was stirred at this temperature for 3 hours and then 500 mL of water was added in portions. The mixture is stirred for 10 minutes, and transferred into a separatory funnel and separated. The aqueous phase was heated at 105° C. for 6 hours. The pH of the solution was brought to 4.3 by adding 50% NaOH. The solution was concentrated half of its volume (250 mL) and stirred for 12 hours at 25° C. The product was collected by filtration washed with 25 mL of cold water, air dried at 25° C. to give 135 g of 4-Amino-1-hydroxbutylidene-1,1-bisphosphonic acid monosodium salt trihydrate as a white solid in 43% yield. After completion of the reaction, the structure of the sunflower oil was checked by $^1$H-NMR and $^{13}$C-NMR and no change was observed. This result showed that the oil can be reused.

EXAMPLE 7

Preparation of 4-Amino-1-hydroxbutylidene-1,1-bisphosphonic acid monosodium salt trihydrate by using recovered sunflower oil.

A 1 L flask was equipped with a mechanical stirrer, thermometer, condenser, and an addition funnel. The system was connected to a caustic scrubber and flushed with nitrogen. The flask was charged with 100 mL of recovered sunflower oil obtained from example 1. The temperature was brought to 75° C. At this temperature, 20 g (0.19 mol) of 4-aminobutyric acid and 15.9 g (0.19 mol) of phosphorous acid were added. The mixture was stirred for 15 minutes. Phosphorous trichloride 26 mL (0.29 mol) was added to this solution in 10 minutes by keeping the internal temperature between 70° C. to 75° C. The mixture was stirred at this temperature for 3 hours and then 100 mL of water was added in portions. The mixture is stirred for 5 minutes, and transferred into a separatory funnel. The phases were separated. The aqueous phase was taken and stirred at 105° C. for 6 hours. The pH of the solution was brought to 4.3 by adding 50% NaOH. The solution was stirred for 12 hours 25° C. The product was collected by filtration, washed with 25 mL of cold water, air dried at 25° C. to give 26.3 g of 4-Amino-1-hydroxbutylidene-1,1-bisphosphonic acid monosodium salt trihydrate as a white solid in 42% yield.

EXAMPLE 8

Preparation of 4-Amino-1-hydroxbutylidene-1,1-bisphosphonic acid monosodium salt trihydrate by using sunflower oil without separation of the phases before hydrolysis.

A 500 mL flask was equipped with a mechanical stirrer, thermometer, condenser, and an addition funnel. The system was connected to a caustic scrubber and flushed with nitrogen. The flask was charged with 50 mL of sunflower oil. The temperature was brought to 75° C. At this temperature 10 g (0.097 mol) of 4-aminobutyric acid and 7.95 g (0.097 mol) of phosphorous acid were added. The mixture was stirred for 15 minutes. Phosphorous trichloride 13 mL (0.145 mol) was added to this solution in 5 minutes by keeping the internal temperature between 70 to 75° C. The mixture was stirred for 3 hours at this temperature and then 50 mL of water was added. The two phases system was stirred at 105° C. for 6 hours and then transferred into a separatory funnel. The aqueous phase was taken. The pH of the solution was brought to 4.3 by adding 50% NaOH. Acetone 25 mL was added to the solution and stirred for 12 hours 25° C. The product was collected by filtration washed with 25 mL of cold water, air dried at 25° C. to give 13.2 g of 4-Amino-1-hydroxbutylidene-1,1-bisphosphonic acid monosodium salt trihydrate as a white solid in 43% yield. The structure of the oil used in this reaction was checked by $^1$H-NMR, the spectra showed some hydrolysis of the triglycerides under reflux condition.

EXAMPLE 9

Preparation of 4-Amino-1-hydroxbutylidene-1,1-bisphosphonic acid monosodium salt trihydrate by using olive oil.

Instead of sunflower oil, olive oil was used as a solvent. The reaction was carried out with a 10 g scale following the procedure described in example 1. After filtration, 9 g of 4-Amino-1-hydroxbutylidene-1,1-bisphosphonic acid monosodium salt trihydrate was obtained as a white solid in 36% yield.

What is claimed is:

1. A process for preparation of 4-amino-1-hydroxybutylidene-1,1-biphosphonic acid or salts thereof, comprising the steps of:
   (a) reacting 4-aminobutyric acid with phosphorous acid and phosphorous trichloride in the presence of aralkyl ethoxylates or alkyl ethoxylates, having the formula of R—X—O—$(CH_2CH_2O)_n$—H, or in the presence of triglycerides selected from the group consisting of plant oils or animal oils, having the formula of $(RCO_2CH_2)_2$CHCOOR, wherein R represents branched or non-branched alkyl groups having 1 to 20 carbon atoms or alkenyl groups having 2 to 20 carbon atoms, n is a number between 1 and 30 and X is a variable which represents phenyl or naphthyl or —$CH_2$— when R is an alkenyl group and which represents phenyl or naphthyl when R is an alkyl group;
   (b) recovering said 4-amino-1-hydroxybutylidene-1,1-biphosphonic acid or salts thereof by an hydrolysis reaction of mono-, di-, tri- or poly phosphorous esters of 4-aminobutyric acid.

2. The process of claim 1, wherein the reaction is conducted in the presence of ethoxylates or triglycerides in which R is an alkyl or alkenyl having 4 to 19 carbon atoms, X is phenyl or —$CH_2$—, and n=4–30.

3. The process of claim 2, wherein the reaction is conducted at a temperature from 40° C. to 150° C.

4. The process of claim 2, wherein the reaction is conducted in the presence of ethoxylates in which R is an alkyl or alkenyl group having 9 carbons, X is phenyl and n is an integer ranging from 4 to 10, wherein the ethoxylate is selected from the group consisting of nonylphenol 4 ethoxylate, nonylphenol 6 ethoxylate and nonylphenol 10 ethoxylate.

5. The process of claim 2, wherein the reaction is conducted in the presence of ethoxylates in which R is an alkenyl group having 11 carbon atoms, X is $CH_2$ and n=6 wherein the ethoxylate is lauryl alcohol with 6 mol ethoxylate.

6. The process of claim 2, wherein the reaction is conducted in the presence of triglycerides in which s is alkyl or alkenyl group having 12 to 20 carbon atoms and containing one or more double bonds, wherein the triglyceride is selected from one or more of the group consisting of sunflower oil, olive oil.

7. The process of claim 4, 5, or 6, wherein the temperature is around 70° C.

8. The process of claim 1, wherein the reaction is conducted at a temperature from 40° C. to 150° C.

9. The process of claim 1, wherein the reaction is conducted in the presence of ethoxylates in which R is an alkyl or alkenyl group having 9 carbons, X is phenyl and n is an integer ranging from 4 to 10, wherein the ethoxylate is selected from the group consisting of nonylphenol 4 ethoxylate, nonylphenol 6 ethoxylate and nonylphenol 10 ethoxylate.

10. The process of claim 1, wherein the reaction is conducted in the presence of ethoxylates in which R is an alkenyl group having 11 carbon atoms, X is $CH_2$ and n=6 wherein the ethoxylate is lauryl alcohol with 6 mol ethoxylate.

11. The process of claim 1, wherein the reaction is conducted in the presence of triglycerides in which R is alkyl or alkenyl group having 12 to 20 carbon atoms and containing one or more double bonds, wherein the triglyceride is selected from one or more of the group consisting of sunflower oil, olive oil and corn oil.

12. The process of claim 9, 10, or 11, wherein the temperature is around 70° C.

13. The process of claim 3, wherein the reaction is conducted in the presence of ethoxylates in which R is an alkyl or alkenyl group having 9 carbons, X is phenyl and n is an integer ranging from 4 to 10, wherein the ethoxylate is selected from the group consisting of nonylphenol 4 ethoxylate, nonylphenol 6 ethoxylate and nonylphenol 10 ethoxylate.

14. The process of claim 3, wherein the reaction is conducted in the presence of ethoxylates in which R is an alkenyl group having 11 carbon atoms, X is $CH_2$ and n=6 wherein the ethoxylate is lauryl alcohol with 6 mol ethoxylate.

15. The process of claim 3, wherein the reaction is conducted in the presence of triglycerides in which R is alkyl or alkenyl group having 12 to 20 carbon atoms and containing one or more double bonds, wherein the triglyceride is selected from one or more of the group consisting of sunflower oil, olive oil and corn oil.

* * * * *